(12) United States Patent
Seakins

(10) Patent No.: US 6,598,604 B1
(45) Date of Patent: Jul. 29, 2003

(54) FAULT PROTECTION SYSTEM FOR A RESPIRATORY CONDUIT HEATER ELEMENT

(75) Inventor: Paul John Seakins, Auckland (NZ)

(73) Assignee: Fisher & Paykel Limited, Auckland (NZ)

( * ) Notice: Subject to any disclaimer, the term of this patent is extended or adjusted under 35 U.S.C. 154(b) by 0 days.

(21) Appl. No.: 09/464,495

(22) Filed: Dec. 15, 1999

(30) Foreign Application Priority Data

Dec. 23, 1998 (NZ) ................................................ 333552

(51) Int. Cl.[7] ............................ A61M 15/00; H05B 3/02
(52) U.S. Cl. ............................ 128/203.17; 128/204.17; 219/481
(58) Field of Search .......... 128/201.13, 202.22–202.24, 128/200.13, 204.17, 204.18, 204.21, 203.12, 203.17, 203.26, 203.27; 219/481, 501, 509, 517, 492, 212, 262, 268, 269; 392/488, 489; 361/93.1, 93.4, 94, 100; 372/311

(56) References Cited

U.S. PATENT DOCUMENTS

| | | | | |
|---|---|---|---|---|
| 4,277,671 A | * | 7/1981 | Mori et al. .................. 219/492 |
| 4,436,986 A | * | 3/1984 | Carlson ....................... 219/212 |
| 4,506,259 A | * | 3/1985 | Rhodes ........................ 340/640 |
| 4,550,359 A | * | 10/1985 | West ............................ 361/56 |
| 4,598,195 A | * | 7/1986 | Matsuo ....................... 219/497 |
| 4,677,281 A | * | 6/1987 | Mills .......................... 219/212 |
| 4,708,831 A | * | 11/1987 | Elsworth et al. ............. 261/130 |
| 4,793,343 A | * | 12/1988 | Cummins, Jr. et al. . 128/204.17 |
| 4,822,983 A | * | 4/1989 | Bremner et al. ............. 219/212 |
| 5,282,107 A | * | 1/1994 | Balakrishnan ............... 361/18 |
| 5,367,146 A | * | 11/1994 | Grunig ........................ 219/497 |
| 5,392,770 A | | 2/1995 | Clawson et al. |
| 5,420,397 A | * | 5/1995 | Weiss et al. ................. 219/492 |
| 5,422,461 A | * | 6/1995 | Weiss et al. ................. 219/212 |
| 5,471,359 A | * | 11/1995 | Simpson et al. ....... 250/227.22 |
| 5,537,996 A | | 7/1996 | McPhee |
| 5,558,084 A | * | 9/1996 | Daniell et al. .......... 128/203.17 |
| 5,583,384 A | | 12/1996 | Henry |
| 5,640,951 A | * | 6/1997 | Huddart et al. ......... 128/204.77 |
| 5,710,408 A | * | 1/1998 | Jones .......................... 219/481 |
| 5,719,493 A | * | 2/1998 | Higashi et al. .............. 219/216 |
| 5,734,543 A | * | 3/1998 | Turner ......................... 361/154 |
| 5,737,165 A | * | 4/1998 | Becker ......................... 361/58 |
| 5,761,020 A | * | 6/1998 | Nadd .......................... 361/103 |
| 5,770,836 A | * | 6/1998 | Weiss .......................... 219/212 |
| 5,801,914 A | * | 9/1998 | Thrash ........................ 219/212 |
| 5,811,765 A | * | 9/1998 | Nakagawa et al. ......... 219/497 |
| 5,818,011 A | * | 10/1998 | Ito et al. ..................... 219/257 |
| 5,847,910 A | | 12/1998 | Efantis et al. |
| 5,861,610 A | * | 1/1999 | Weiss .......................... 219/212 |
| 5,988,164 A | * | 11/1999 | Paluch .................. 128/203.26 |
| 6,050,260 A | * | 4/2000 | Daniell et al. .......... 128/204.22 |
| 6,100,510 A | * | 8/2000 | Chen et al. ................. 219/497 |
| 6,107,611 A | * | 8/2000 | Jones .......................... 219/509 |
| 6,142,963 A | * | 11/2000 | Black et al. .................. 601/56 |
| 6,310,332 B1 | * | 10/2001 | Gerrard ....................... 219/212 |

FOREIGN PATENT DOCUMENTS

| | | |
|---|---|---|
| FR | 2590749 | 5/1987 |
| WO | 8605651 | 9/1986 |

* cited by examiner

Primary Examiner—Weilun Lo
Assistant Examiner—Teena Mitchell
(74) Attorney, Agent, or Firm—Trexler, Bushnell, Giangiorgi, Blackstone & Marr, Ltd.

(57) ABSTRACT

A fault protection circuit for a respiratory conduit heater element in a respirator humidification system is disclosed. The circuit includes a spark detector as well as overcurrent detector. Several variations are included for the spark detector including a two winding transformer, a center tapped two winding transformer), and a high pass filtered inductor. A semiconductor switching configuration is also disclosed. Once the protection circuit detects a change in current over a certain level, or the average level raises above a threshold, then the current in the heater element is interrupted for a preset period.

16 Claims, 4 Drawing Sheets

FAULT PROTECTION SYSTEM FOR A RESPIRATORY CONDUIT HEATER ELEMENT

BACKGROUND OF THE INVENTION (1) Field of the Invention

This invention relates to respiratory humidifiers and heated breathing conduits used to couple a patient to the humidifier. A fault protection system for the conduit heater wire is disclosed.

(2) Description of the Prior Art

In order to supply gases to a patient or a person needing such gases, it may sometimes be necessary to first humidify those gases, for example using a respiratory humidifier/ventilator system. In such a case where the gases have been humidified, and therefore laden with water, it is likely that during transport through a conduit to the patient, condensation of that water vapour will occur. In order to overcome this disadvantage it is known to associate a heater wire with respiratory humidifier breathing conduits to avoid condensation. Examples of such a heated breathing conduit are disclosed in U.S. Pat. No. 5,537,996 (McPhee) and U.S. Pat. No. 5,392,770 (Clawson et al.).

However there are safety concerns with using a heated wire system, especially when the gas in the breathing conduit contains a high concentration of oxygen, which may be a common condition in hospitals. It is possible for ignition of the heater wire and conduit materials to occur if certain fault conditions are present. Thus physicians may be hesitant to use a humidifier with an associated heater wire, due to the perceived risks to the patient. However if the a humidifier is not used various respiratory problems can occur due to the lack of controlled humidity.

BRIEF SUMMARY OF THE INVENTION

It is an object of the present invention to provide a fault protection system for a respiratory conduit heater element which goes some way towards overcoming the abovementioned disadvantages.

Accordingly, in a first aspect, the present invention consists in a fault protection system for a respiratory conduit heater element comprising:

detecting means which include means to detect a rapid change of current in said heater element, current interruptor means in series with said heater element, and timer means adapted to control the action of said interruptor means and thereby in use determining the duration of current interruption, said timer means being triggered by said detecting means.

In a second aspect, the present invention consists in a semiconductor switching circuit for rapidly controlling the AC supply current through a load from a power supply comprising:

two same channel MOSFETs connected in series with their source and gate electrodes respectively tied together, said circuit adapted to receive a switching voltage between the commoned gate and source electrodes, their drain electrodes adapted to be connected to a load and a power supply respectively.

In a third aspect, the present invention consists in a semiconductor switching circuit for rapidly controlling the AC supply current through a load from a power supply comprising:

two same channel MOSFETs connected in series with their drain and gate electrodes respectively tied together, said circuit adapted to receive a switching voltage between the commoned gate and drain electrodes, their source electrodes adapted to be connected to a load and a power supply respectively.

In a fourth aspect, the present invention consists in a fault protection system for a respiratory conduit heater element comprising:

a detector means which includes a peak current detector for detecting current in the heater element a current interruptor in series with said heater element, and a timing circuit adapted to control the action of said current interruptor and thereby in use determining the duration of current interruption, said timing circuit being triggered by said detector, when a predetermined threshold current is exceeded.

In a fifth aspect, the present invention consists in a respiratory humidification system wherein a conduit connects a patient to a humidifier, said conduit being heated by a respiratory conduit heater element controlled by said humidifier, the improvement comprising that said humidifier includes a fault protection system for said heater element comprising:

detecting means which include means to detect a rapid change of current in said heater element, current interruptor means in series with said heater element, and timer means adapted to control the action of said interruptor means and thereby in use determining the duration of current interruption, said timer means being triggered by said detecting means.

In a sixth aspect, the present invention consists in a respiratory humidification system wherein a conduit connects a patient to a humidifier, said conduit being heated by a respiratory conduit heater element controlled by said humidifier, the improvement comprising that said humidifier includes a fault protection system for said heater element comprising:

detecting means which includes a peak current detector for detecting current in the heater element current interruptol means in series with said heater element, and timer means adapted to control the action of said interruptor means and thereby in use determining the duration of current interruption, said timer means being triggered by said detecting means, when a predetermined threshold current is exceeded.

BRIEF DESCRIPTION OF THE DRAWINGS

Preferred forms of the invention will now be described with reference to the accompanying drawings.

DETAILED DESCRIPTION

Figure 1:
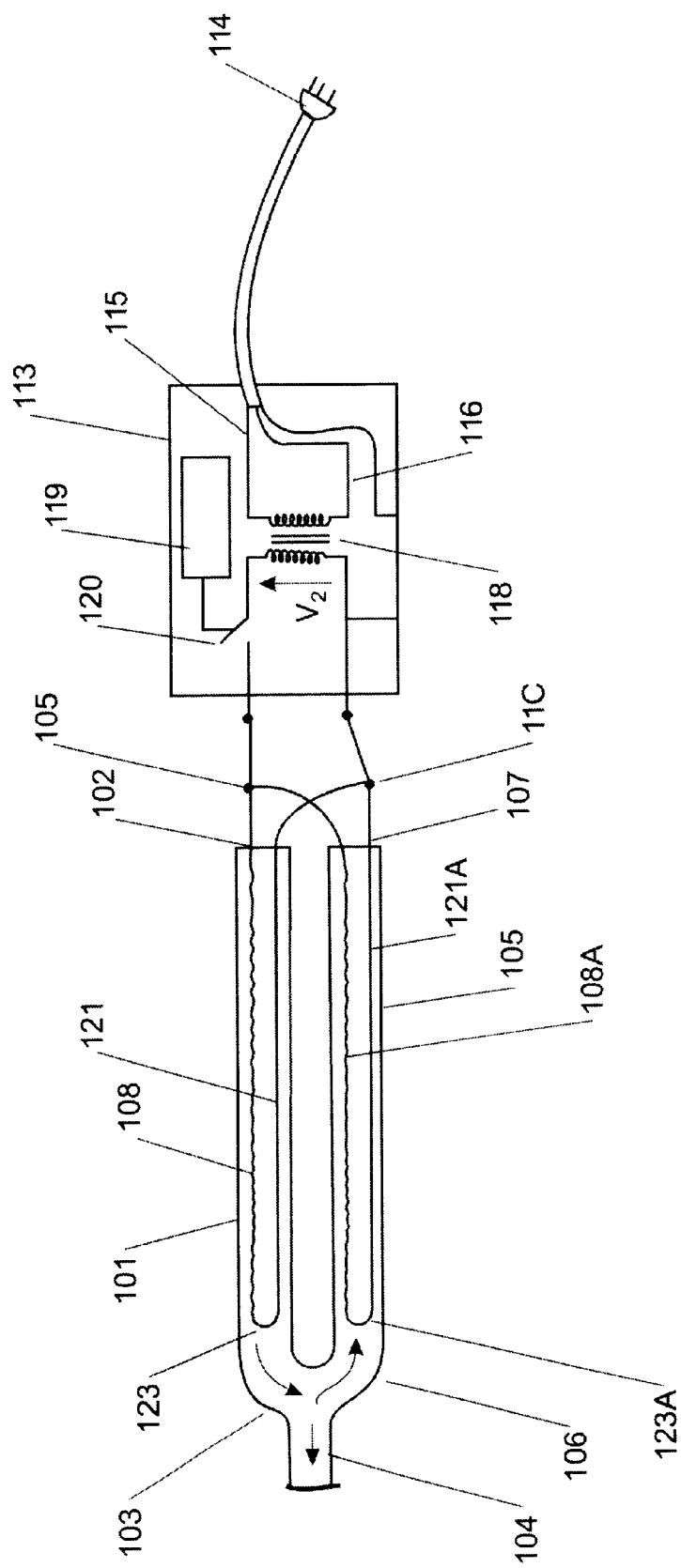
FIG. 1 is a schematic of a prior art heated breathing conduit to be used with a respiratory humidifier.

An example of a prior art heated breathing conduit 102 for use with a respiratory humidifier/ventilator, is shown generally in FIG. 1. The heated breathing conduit ordinarily comprises an inspiratory conduit 101 connected at its proximal end 102 to the gases outlet of a respiratory humidifier (not shown) and at its distal end 103 to a "Y" shaped connector having three inlet/outlet ports. One port 104 of the "Y" shaped connector directs the inspiratory gases to the patient and also receives exhaled air from the patient. The expired air is channelled by the "Y" shaped connector to an expiratory conduit 105 via the third port 106 of the "Y" shaped connector so that the expiratory gases may be returned to the humidifier/ventilator (not shown) from the end 107 of the expiratory conduit 105.

The conduits 101,105 are heated by a heater wire 108 located within the inspiratory conduit 101 and a second heater wire 108A is located within the expiratory conduit 105. In this example the two heater wires are configured in parallel such that the second heater wire 108A shares connection 109 with the first heater wire 108 and is connected at point 123A to the second earth return conductor 121A which extends from point 123A to connection 110, although other arrangements are equally possible.

Power is supplied via standard domestic or industrial supply 114. The heater wire 108 is supplied with power from the secondary side of a step down transformer 118 which is connected to the external voltage supply across the phase 115 and neutral 116 conductors. A controller 119 controls a switch 120 which, when closed, energises the heater wire.

The controller can determine if there is no heater wire connected, and provides an audible alarm if this is detected.

As with all electrical installations there exists fault conditions which potentially can ignite a fire. Trials have indicated that two fault conditions in particular appear to be especially important in starting a fire in a heated respiratory conduit. These are:

1. A break in the heater wire, leading to repeated sparks which cause ignition
2. Excessive current in the breathing circuit, leading to melting or ignition of the breathing circuit materials. This can be caused by incorrect breathing circuit design or assembly, or by a short circuit.

The present invention may be retrofitted to existing respiratory humidifier/ventilator systems or included as part of the humidifier controller. It detects sparking and over current in the heating wire 103 as detailed in the following embodiments.

According to the present invention spark detection is accomplished by detecting the rapid change in current that occurs following disconnection of the heater wire load. An inductor is used because a rapid change in current induces a voltage spike across the inductor, which can easily be detected. Since sparks (or disconnections of the heater wire) can happen at any part of the mains cycle (including those times when the mains voltage is near zero) the spark detection circuitry cannot hope to pick up every single spark. In practice though disconnections which occur near the mains zero voltage do not have significant energy for ignition. It is practical to detect 75% of all heater wire disconnections, and this provides the required degree of safety.

Figure 2:
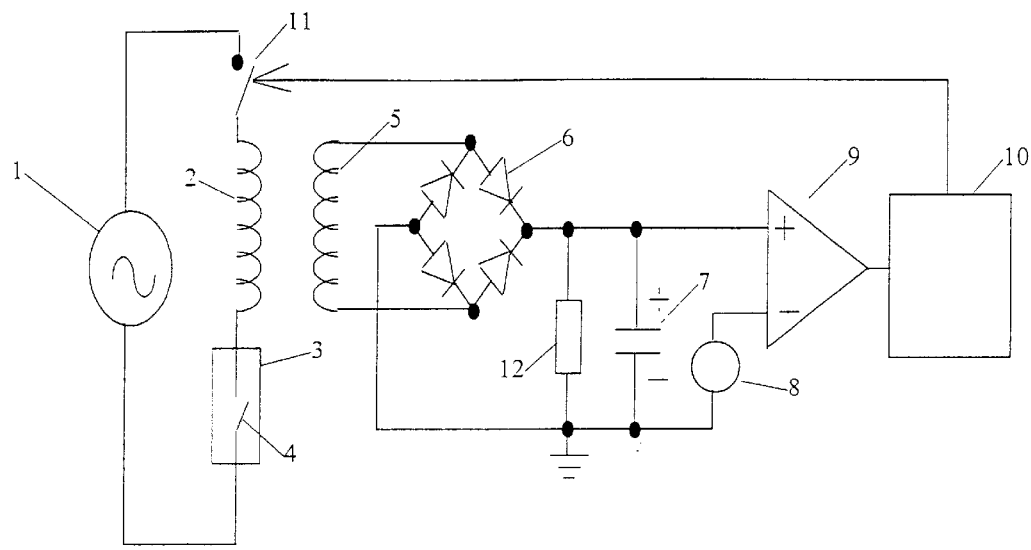
FIG. 2 is a block diagram of a spark detector using a two winding transformer.

In a first embodiment of the invention a two winding transformer is connected in series with the heater wire. As can be seen in FIG. 2 during normal operation the current flows from the AC supply 1 through the primary 2 of the spark detection transformer then through the heater wire 3. If a break 4 occurs in the heater wire 3 (causing sparking), a rapid change in current will occur in the heater wire 3. Any rapid change in current through the primary winding 2 of the transformer creates a voltage spike, due to the action of its inductance. The voltage spike is passed onto the secondary winding 5 of the transformer and is multiplied by the turns ratio.

The voltage spike on the secondary winding may be either positive or negative, but the four diodes form a bridge rectifier 6, so that the voltage spike always charges the capacitor 7 with a positive voltage. If the magnitude of the voltage spike is large enough, then the capacitor will charge above the threshold voltage 8 of the comparator 9, which causes the output of the comparator 9 to go high, enabling the timer 10. This comparator drives a timer 10 which turns off the power to the heater wires for a period of time (e.g several seconds) using a switching circuit 11. The resistor 12 across the capacitor 7 allows the voltage to decay away to zero if no sparks are detected.

Figure 3:
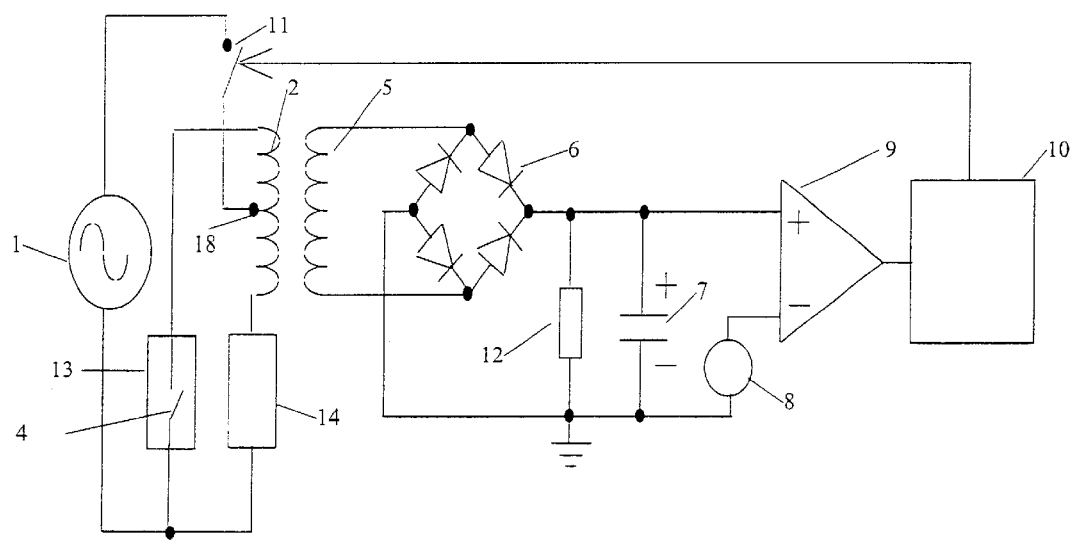
FIG. 3 is a block diagram of a spark detector using a two winding transformer with a centre tapped primary.

In a second embodiment a two winding transformer with a center tapped primary winding is connected in series with the heater wire. In order to reject mains voltage spikes as a source of false triggering, the primary winding can be center tapped 18 as shown in FIG. 3, and the currents from the inspiratory 13 and expiratory 14 heater wires are each passed through a different half of the primary winding. In this way, the current of any mains borne interference passes through both halves of the primary winding, and the resultant magnetic fields (flowing through the core of the transformer) cancel out. A spark 4 will only occur in one heater wire limb at a time (shown here as the inspiratory 13), and therefore is not cancelled out. The remainder of the circuit operates in the same way as the first embodiment, with the capacitor 7 voltage compared against a threshold 8, and the comparator 9 driving a timer 10.

Figure 4:
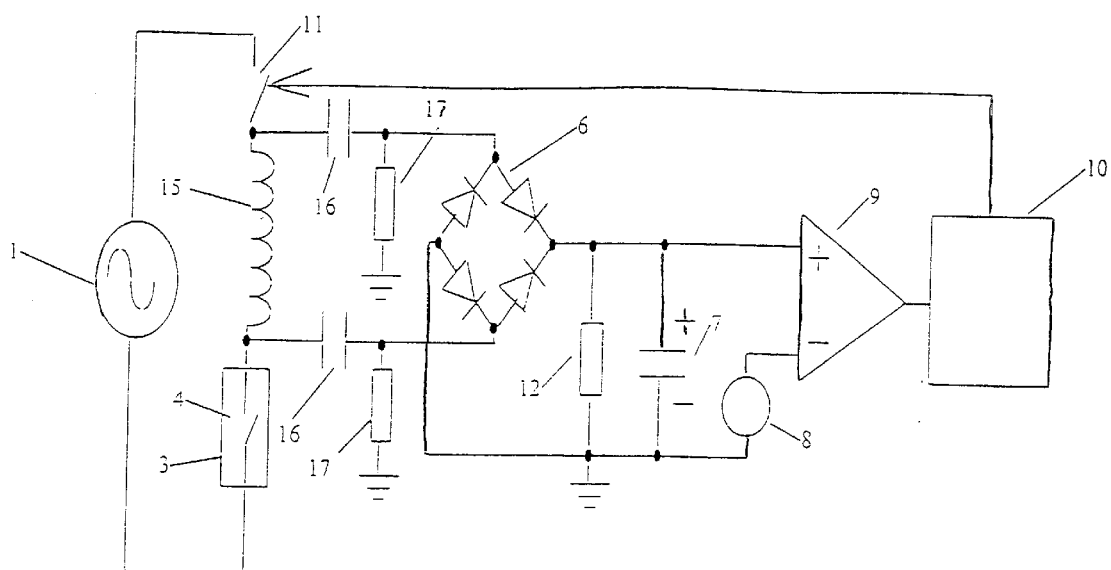
FIG. 4 is a block diagram of a spark detector using a single coil and high pass filter.

In a third embodiment shown in FIG. 4, as an alternative to using a transformer a coil 15 is connected in series with the heater wire 3. The coil 15 is used instead of the transformer primary utilised in the fist and second embodiments. A high pass filter (resistors 17 and capacitors 16) is used to reject mains e.g.: 50–60 Hz frequencies. The remainder of the circuit operates in the same way as the first embodiment. Similarly to the first embodiment this embodiment does not include specific rejection of mains borne interference e.g.: spikes. However variations in this embodiment can be envisaged which do incorporate rejection of mains borne interference.

The technique used for detecting excess current is common to all three embodiments of the invention described above. The threshold for current detection is set to be the maximum current that will be drawn by the lowest foreseeable resistance heater wire, at the highest rated mains voltage +10%. The current detector is designed to respond to the peak current instead of the average current for two reasons : (a) peak current is faster responding than average, (b) the peak current is independent of the duty cycle that the controlling humidifier is supplying.

Figure 5:
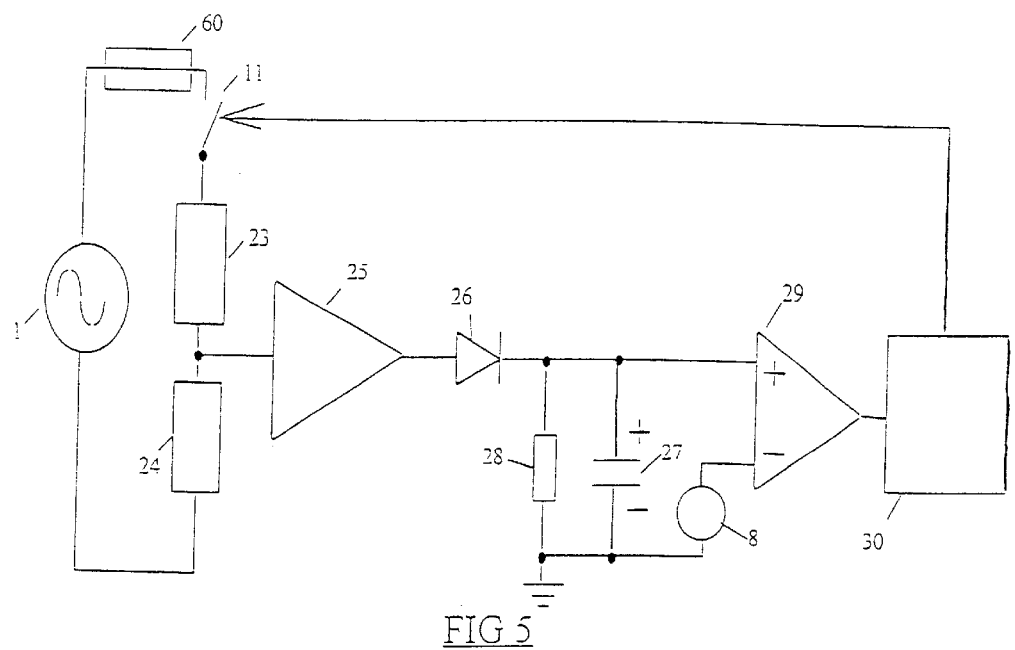
FIG. 5 is a block diagram of a current level detector.

Referring to FIG. 5 the heater wire current to be measured is passed through a low value resistor 24. The voltage which appears across the resistor is proportional to the current flowing in the heater wire 23. This voltage is passed through an amplifier 25, then passes to a peak detection circuit, where a capacitor 27 is charged up by a diode 26 to the maximum peak of the AC voltage. If the peak voltage is higher than the threshold voltage 8 then the comparator 29, operates a timer 30, which removes power from the heater wire for a period of time. At the end of this time period the current is restored, but if the current is still too high then the peak is detected very quickly and power removed again. Using this circuit, a completely short-circuited heater wire can be tolerated without blowing the heater base fuse 60. The resistor 28 slowly discharges the capacitor.

The control strategy for all faults involves disconnecting the power from the heater wire for a period and then reapplying it. This is to avoid shutting the system down in response to a non critical event.

Common to all embodiments of spark detection is the control strategy used for removing and reapplying power to the heater. The timing circuit (10) must operate for long enough that any heat that is generated by a spark has time to dissipate before the heater wire power is reapplied. In practice a time period of 1 second has been found to be sufficient. As a further aspect, the timing circuit could also be made to count up the number of sparks detected, and then disconnect the heater wire permanently. This is to discriminate against one of the heater wires being disconnected while the system is in use.

If overcurrent is detected, then the average power being dissipated in the heater wire is determined by the time period that the device takes to detect the high current (the "on" time) and the period that the current is removed ("off"). With the circuit described, the maximum time it will take to detect a high peak current is one AC cycle (i.e. 20 msec at 50 Hz). So long as the "off" time is many times longer than the "on" time then the heater wire will not dissipate excessive power and will be safe. In the preferred embodiment the heater wire is turned off for 2 secs, so power is applied for less than 1% of the time.

The 'off' time period should be more than, say, 10 mains cycles to avoid the power dissipated getting too high. Also it should not be too long otherwise the operator loses the useful alarm feedback. For instance an operator removing the faulty heater wire would expect the humidifier heater wire alarm condition to cancel promptly. Too long a period may confuse the operator.

Of importance to both spark detection and current detection is the ability to disconnect the heater wire quickly when one of these conditions is detected. Conventionally a triac is used to switch off current in an AC circuit such as this, but triacs cannot be turned off instantly—turn off occurs at the AC zero crossing, which may take up to 10 msec at 50 Hz mains. Triacs also have a 1–2 V saturation voltage, which results in power loss. This is to allow the user to connect or disconnect the heater wires a limited number of times without causing a permanent disconnection or audible alarm. However, repeated sparks would cause this to occur.

Another prior art alternative (shown in FIG. 6) is to use an N-channel MOSFET 31 with a separate substrate connection 32. MOSFETs have a very fast switching time (less than 1 microsecond). They can also have a very low "on" resistance (e.g 0.03 ohm) which results in very low power dissipation. However a single MOSFET configuration has two disadvantages. Firstly, it requires a MOSFET with a separate connection to the substrate, instead of having the substrate 32 connected to the source 35. Secondly, the substrate 32 must be connected to a bias voltage 36 which is more negative than the peak negative AC voltage (from the source 39) that will be switched. This is necessary because the construction of a MOSFET involves two intrinsic diodes 37,38 between the substrate 32 and the drain 34 and source 35. If these diodes 37,38 are not kept reverse biased then they will conduct, and the switching action of the MOSFET 31 will be lost. The negative voltage 36 applied to the substrate 32 keeps these diodes 37,38 reverse biased.

Figure 7:
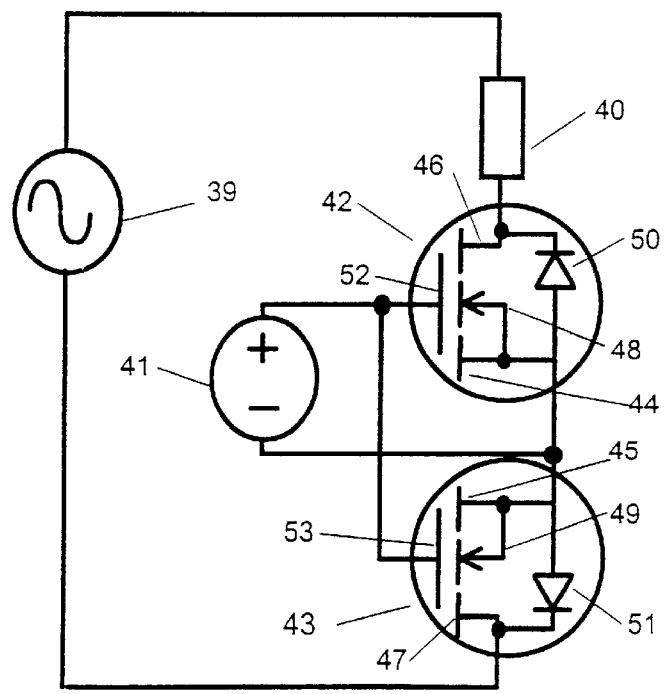
FIG. 7 is a circuit diagram of a pair of back to back MOSFETs used for switching the heater wire.

In the preferred embodiment of this invention (shown in FIG. 7) the heater wire 40 is switched by two back to back N-channel MOSFETs 42,43 which have their source connections 44,45 connected together. The MOSFETs have their substrates 48,49 internally connected to their source leads, as is common. As previously described there are intrinsic diodes 50,51 connected between the source (substrate) and the drain of each MOSFET. These diodes are connected back-to-back and do not conduct. The gates 52,53 of both MOSFETs are connected together, and a voltage 41 is applied between the gate connections 52,53 and the source connections 44,45 to turn the MOSFETs on and off.

To turn the AC current off the gate-source voltage 41 is set to zero, and the MOSFETs stop conducting. To turn the current on, the gate-source voltage is increased above the threshold voltage of the MOSFET, and they conduct. In the preferred embodiment of the invention the "on" resistance is chosen such that at the highest rated current the drain-source voltage of the MOSFETs never exceeds 0.6V, so that the intrinsic diodes are never allowed to conduct.

Figure 6:
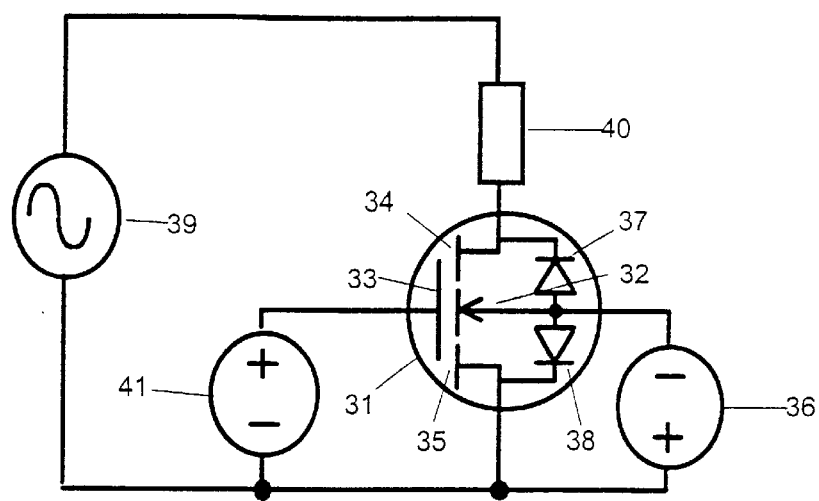
FIG. 6 is a circuit diagram of a prior art single MOSFET switching circuit.

This AC switching configuration overcomes the disadvantages of the AC switch in FIG. 6, while still providing a rapid switching time. By using two MOSFETs connected in reverse the intrinsic diodes cannot conduct, without the use of an external negative bias voltage. Also a separate substrate connection is not required on the MOSFETs.

What is claimed is:

1. A fault protection system adapted for use with a heater element comprising:

detecting means which include means to detect a rapid change in current in said heater element, current interruptor means adapted to be in series with said heater element, and timing means configured to activate said current interruptor means to interrupt the current in the heater element when said rapid change in current exceeds a first predetermined threshold.

2. A fault protection system adapted for use with a heater element, as claimed in claim 1 wherein said current interruptor means comprises:

two same channel MOSFETS each including a source, a gate and a drain, and with the source and gate of each said MOSFET respectively connected together, and adapted to receive a common switching voltage between each gate and source.

3. A fault protection system adapted for use with a heater element, as claimed in any one of claims 1 to 2 wherein said timing means is configured to activate said current interruptor means to interrupt the current in the heater element for a predetermined period.

4. A fault protection system adapted for use with a heater element comprising:

detecting means which includes a peak current detector for detecting peak current in said heater element and means to detect a rapid change in current in said heater element, current interruptor means adapted to be in series with said heater element, and timing means configured to activate said current interruptor means to interrupt the current in said heater element when said rapid change in current exceeds a first predetermined threshold and configured to activate said current interruptor means to interrupt the current in said heater element when said peak current exceeds a second predetermined threshold.

5. A fault protection system adapted for use with a heater element as claimed in claim 2, wherein said detecting means comprises:
   a transformer including a primary and secondary winding, said primary winding adapted to be connected in series with the heater element and a power source,
   a full wave rectifier including rectifier input means and rectifier output means, said rectifier input means connected across said secondary winding of said transformer,
   a low pass filter including low pass filter input means and low pass filter output means, said low pass filter output means providing a low pass filter output, said low pass filter input means connected to said rectifier output means, and
   a comparator including comparator input means and comparator output means, said comparator input means connected to said low pass filter output means, wherein said low pass filter output reaches said first predetermined threshold, said current interruptor means is activated to interrupt the current in said heater element.

6. A fault protection system adapted for use with a heater element as claimed in claim 4, wherein said detecting means comprises:
   a transformer including a primary winding with at least two end and a center tap and secondary winding, each end of said primary winding adapted to be connected with a first circuit of said heater element and a second circuit of said heater element respectively and said center tap of said primary winding adapted to be connected to a power source,
   a full wave rectifier including rectifier input means and rectifier output means, said rectifier input means connected across said secondary winding of said transformer,
   a low pass filter including low pass filter input means and low pass filter output means, said low pass filter output means providing a low pass filter output, said low pass filter input means connected to said rectifier output means, and
   a comparator including comparator input means and comparator output means, said comparator input means connected to said filter output means, wherein said low pass filter output reaches said first predetermined threshold, said current interruptor means is activated to interrupt the current in said heater element.

7. A fault protection system adapted for use with a heater element as claimed in claim 2, wherein said detecting means comprises:
   an inductor having first and second ends where said first end of said inductor being adapted to be connected with one end of said heater element and said second end of said inductor adapted to be connected to a power source,
   a first high pass filter including first filter input means and first filter output means, said first filter input means connected to said first end of said inductor,
   a second high pass filter including second filter input means and second filter output means, said second filter input means connected to said second end of said inductor,
   a full wave rectifier including rectifier input means and rectifier output means, said rectifier input means connected to said first filter output means and said second filter output means respectively,
   a low pass filter including low pass filter input means and low pass filter output means, said low pass filter output means providing a low pass filter output, said low pass filter input means connected to said rectifier output means, and
   a comparator including comparator input means and comparator output means, said comparator input means connected to said low pass filter output means, wherein said low pass filter output reaches said first predetermined threshold, said current interruptor means is activated to interrupt the current in said heater element.

8. A fault protection system adapted for use with a heater element comprising:
   detecting means which includes a peak current detector for detecting peak current in said heater element,
   current interruptor means adapted to be in series with said heater element, and
   timing means configured to activate said current interruptor means to interrupt said current in the heater element when said peak current exceeds a predetermined threshold.

9. In a respiratory humidification system wherein a conduit supplies humidified gases to a patient from a humidifier, said conduit or said gases being heated by a respiratory conduit heater element, the improvement comprising that said system includes a fault protection system for said heater element comprising:
   detecting means which include means to detect a rapid change of current in said heater element,
   current interruptor means in series with said heater element, and
   timing means configured to activate said current interruptor means to interrupt the current in said heater element when said rapid change in current exceeds a first predetermined threshold.

10. In a respiratory humidification system as claimed in claim 9 the improvements further comprising that said current interruptor means comprises:
   two same channel MOSFETS each including a source, a gate and a drain with the source and gate of each said MOSFET respectively connected together, and adapted to receive a common switching voltage between each gate and source.

11. In a respiratory humidification system as claimed in any one of claims 9 to 10, the improvements further comprising said timing means is configured to activate said current interruptor means to interrupt the current in said heater element for a predetermined period.

12. In a respiratory humidification system wherein a conduit humidified gases to a patient from a humidifier, said conduit or said gases being heated by a respiratory conduit heater element, the improvements comprising that said system includes a fault protection system for said heater element comprising:
   detecting means which includes a peak current detector for detecting a peak current in said heater element and means to detect a rapid change in current in said heater element,
   current interruptor means adapted to be in series with said heater element, and
   timing means configured to activate said current interruptor means to interrupt the current in said heater element when said rapid change in current exceeds a first predetermined threshold and configured to activate said current interruptor means to interrupt the current in said heater element when said peak current exceeds a second predetermined threshold.

13. In a respiratory humidification system as claimed in claim 12, the improvements further comprising that said detecting means comprises:

a transformer including a primary and secondary winding, said primary winding adapted to be connected in series with said heater element and a power source, a full wave rectifier including rectifier input means and rectifier output means, said rectifier input means connected across said secondary winding of said transformer, a low pass filter including low pass filter input means and low pass filter output means, said low pass filter output means providing a low pass filter output, said low pass filter input means connected to said rectifier output means, and a comparator including comparator input means and comparator output means, said comparator input means connected to said low pass filter output means, wherein said low pass filter output reaches said first predetermined threshold, said current interruptor means is activated to interrupt the current in said heater element.

14. In a respiratory humidification system as claimed in claim 12, the improvements further comprising that said heater element including a first circuit and a second circuit and said detecting means comprises:

a transformer including a primary winding with at least two ends and a center tap and secondary winding, said primary winding having ends, each end of said primary winding adapted to be connected with a first circuit of said heater element and a second circuit of said heater element respectively and said center tap of said primary winding adapted to be connected to a power source, a full wave rectifier including rectifier input means and rectifier output means, said rectifier input means connected across said secondary winding of said transformer, a low pass filter including low pass filter input means and low pass filter output means, said low pass filter output means providing a low pass filter output, said low pass filter input means connected to said rectifier output means, and a comparator including comparator input means and comparator output means, said comparator input means connected to said low pass filter output means, wherein the low pass filter output reaches said first predetermined threshold, said current interruptor means is activated to interrupt the current in said heater element.

15. In a respiratory humidification system as claimed in claim 12, the improvements further comprising that said detecting means comprises:

an inductor having first and second ends where said first end of said inductor being adapted to be connected with one end of said heater element and said second end of said inductor adapted to be connected to a power source, a first high pass filter including first filter input means and first filter output means, said first filter input means connected to said, first end of said inductor, a second high pass filter including second filter input means and second filter output means, said second filter input means connected to said second end of said inductor, a full wave rectifier including rectifier input means and rectifier output means, said rectifier input means connected to said first filter output means and said second filter output means respectively, a low pass filter including low pass filter input means and low pass filter output means, said low pass filter output means providing a low pass filter output, said low pass filter input means connected to said rectifier output means, and a comparator including comparator input means and comparator output means, said comparator input means connected to said low pass filter output means, wherein said low pass filter output reaches said first predetermined threshold, said current interruptor means is activated to interrupt the current in said heater element.

16. In a respiratory humidification system wherein a conduit delivers humidified gases to a patient from a humidifier, said conduit being heated by a respiratory conduit heater element, the improvement comprising that said system includes a fault protection system for said heater element comprising:

detecting means which includes a peak current detector for detecting peak current in said heater element, current interruptor means in series with said heater element, and timing means configured to activate said current interruptor means to interrupt the current in said heater element when said peak current exceeds a predetermined threshold.

* * * * *

UNITED STATES PATENT AND TRADEMARK OFFICE
CERTIFICATE OF CORRECTION

PATENT NO. : 6,598,604 B1
DATED : July 29, 2003
INVENTOR(S) : Paul John Seakins

It is certified that error appears in the above-identified patent and that said Letters Patent is hereby corrected as shown below:

Title page,
Item [54], Title, "FAULT PROTECTION SYSTEM FOR A RESPIRATORY CONDUIT HEATER ELEMENT" should be -- FAULT PROTECTION SYSTEM --

Column 2,
Line 44, "interruptol" should be -- interruptor --

Signed and Sealed this

Twenty-first Day of December, 2004

JON W. DUDAS
*Director of the United States Patent and Trademark Office*